United States Patent
Vahala et al.

(10) Patent No.: US 9,662,512 B2
(45) Date of Patent: May 30, 2017

(54) MAGNETIC RESONANCE GUIDED LINAC (71) Applicant: KONINKLIJKE PHILIPS N.V., Eindhoven (NL)

(72) Inventors: Erkki Tapani Vahala, Vantaa (FI); Mika Petri Ylihautala, Vantaa (FI); Tero Jouko Valtter Virta, Vantaa (FI); Romhild Martijn Hoogeveen, Best (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/427,524

(22) PCT Filed: Sep. 16, 2013

(86) PCT No.: PCT/EP2013/069149
§ 371 (c)(1),
(2) Date: Mar. 11, 2015

(87) PCT Pub. No.: WO2014/044635
PCT Pub. Date: Mar. 27, 2014

(65) Prior Publication Data
US 2015/0224341 A1 Aug. 13, 2015

Related U.S. Application Data (60) Provisional application No. 61/702,284, filed on Sep. 18, 2012.

(30) Foreign Application Priority Data

Sep. 18, 2012 (EP) .................................. 12184801

(51) Int. Cl.
*A61N 5/10* (2006.01)
*G01R 33/48* (2006.01)
(Continued)

(52) U.S. Cl.
CPC ............ *A61N 5/1049* (2013.01); *A61B 5/055* (2013.01); *A61N 5/10* (2013.01); *A61N 5/1045* (2013.01);
(Continued)

(58) Field of Classification Search
CPC .. A61N 5/1049; A61N 5/1045; A61N 5/1081; A61N 2005/1055;
(Continued)

(56) References Cited

U.S. PATENT DOCUMENTS

2003/0086526 A1* 5/2003 Clark ................... A61B 6/4233
378/64
2008/0212737 A1* 9/2008 D'Souza .............. A61N 5/1049
378/65

(Continued)

FOREIGN PATENT DOCUMENTS

WO 2004024235 A1 3/2004
WO 2010018476 A2 2/2010
(Continued)

OTHER PUBLICATIONS

Of Logier et al., Optical fibre sensors embedded into technical textile for a continuous monitoring of patients under magnetic resonance imaging, 30th Annual International IEEE EMBS Conference Vancouver, British Columbia, Canada, Aug. 20-24, 2008.*

*Primary Examiner* — Bo J Peng (57) ABSTRACT

The invention provides for a medical instrument (200, 300, 400, 500, 502, 600, 700, 702, 800, 802) comprising a LINAC guided by a magnetic resonance imaging system (204). Execution of the instructions by processor to controlling the medical instrument cause the processor to: receive (100) a treatment plan (260) for irradiating the target zone; modify (102) the treatment plan in accordance with an X-ray transmission model of an accessory; acquire (104) magnetic resonance data using the magnetic resonance imaging sys-
(Continued)

tem; reconstruct (106) a magnetic resonance image (268) from the magnetic resonance data; register (108) a location (272) of the target zone in the magnetic resonance image; generate (110) control signals (274) in accordance with the location of the target zone and the X-ray transmission model; and control (112) the LINAC to irradiate the target zone using the control signals.

19 Claims, 6 Drawing Sheets (51) Int. Cl.
| | |
|---|---|
| A61B 5/055 | (2006.01) |
| G01R 33/30 | (2006.01) |
| G01R 33/34 | (2006.01) |
| G01R 33/385 | (2006.01) |
| G01R 33/56 | (2006.01) |

(52) U.S. Cl.
CPC ......... *A61N 5/1064* (2013.01); *A61N 5/1081* (2013.01); *G01R 33/307* (2013.01); *G01R 33/34* (2013.01); *G01R 33/385* (2013.01); *G01R 33/4808* (2013.01); *G01R 33/56* (2013.01); *A61N 5/1065* (2013.01); *A61N 5/1069* (2013.01); *A61N 2005/1051* (2013.01); *A61N 2005/1055* (2013.01); *A61N 2005/1091* (2013.01); *A61N 2005/1094* (2013.01)

(58) Field of Classification Search
CPC ............ A61N 2005/1091; A61B 5/055; G01R 33/4808; G01R 33/34; G01R 33/385; G01R 33/307; G01R 33/56
See application file for complete search history.

(56) References Cited

U.S. PATENT DOCUMENTS

| | | | |
|---|---|---|---|
| 2011/0118588 A1* | 5/2011 | Komblau | A61N 5/1049 600/411 |
| 2011/0130614 A1 | 6/2011 | Schulz | |
| 2011/0142202 A1* | 6/2011 | Brown | A61N 5/1049 378/65 |
| 2011/0196226 A1* | 8/2011 | Gross | A61B 5/055 600/411 |
| 2013/0218000 A1* | 8/2013 | Coppens | A61B 5/004 600/411 |

FOREIGN PATENT DOCUMENTS

| | | |
|---|---|---|
| WO | 2011042820 A1 | 4/2011 |
| WO | 2012063162 A1 | 5/2012 |
| WO | 2012080948 A1 | 6/2012 |

* cited by examiner

MAGNETIC RESONANCE GUIDED LINAC

CROSS-REFERENCE TO PRIOR APPLICATIONS

This application is the U.S. National Phase application under 35 U.S.C. §371 of International Application No. PCT/EP2013/069149, filed on Sep. 16, 2013, which claims the benefit of U.S. Provisional Patent Application No. 61/702,284 and European Patent Application No. 12184801.4, both filed on Sep. 18, 2012. These applications are hereby incorporated by reference herein.

TECHNICAL FIELD

The invention relates to magnetic resonance guided LINACs, in particular to the use of models to compensate for or correct for X-ray transmission through radio frequency coils.

BACKGROUND OF THE INVENTION

In standard Magnetic Resonance Imaging (MRI) systems, the posterior and anterior coils needed for signal reception from the patient, are placed around the patient and travel with the patient. This means that these coils can have a different position every time the patient is being examined. For a Magnetic Resonance (MR) imaging system combined with a LINAC (Linear Accelerator) or MR-LINAC, the radiation beams from the LINAC can potentially harm the RF coils and RF coil electronics. Coils can be designed such that they are less sensitive to radiation beams. By having too many degrees of freedom in coil placement, it can become difficult to design a coil that is insensitive for radiation in all cases.

SUMMARY OF THE INVENTION

The invention provides for a medical instrument and a computer program product in the independent claims. Embodiments are given in the dependent claims.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network. Computer executable code embodied on a computer readable medium may be transmitted using any appropriate medium, including but not limited to wireless, wireline, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. 'Computer storage' or 'storage' is a further example of a computer-readable storage medium. Computer storage is any non-volatile computer-readable storage medium. In some embodiments computer storage may also be computer memory or vice versa.

A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object oriented programming language such as Java, Smalltalk, C++ or the like and conventional procedural programming languages, such as the "C" programming language or similar programming languages and compiled into machine executable instructions. In some instances the computer executable code may be in the form of a high level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It will be understood that each block or a portion of the blocks of the flowchart, illustrations, and/or block diagrams, can be implemented by computer program instructions in form of computer executable code when applicable. It is further under stood that, when not mutually exclusive, combinations of blocks in different flowcharts, illustrations, and/or block diagrams may be combined. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, gear sticks, steering wheel, pedals, wired glove, dance pad, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bistable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

Magnetic Resonance (MR) data is defined herein as being the recorded measurements of radio frequency signals emitted by atomic spins by the antenna of a Magnetic resonance apparatus during a magnetic resonance imaging scan. Magnetic resonance data is an example of medical image data. A Magnetic Resonance Imaging (MRI) image is defined herein as being the reconstructed two or three dimensional visualization of anatomic data contained within the magnetic resonance imaging data. This visualization can be performed using a computer. A portion of magnetic resonance data may also refer to a "shot." Navigator data is an example of magnetic resonance data, and is typically representative of a subject's location or state of motion.

In one aspect the invention provides for a medical instrument comprising a LINAC or linear accelerator with an X-ray source for directing X-ray/gamma radiation at a target zone. The LINAC is adapted for rotating the X-ray source about an axis. Typically LINACs are mounted on a gantry which is able to rotate about an axis. The medical instrument further comprises a magnetic resonance imaging system for acquiring magnetic resonance data with one or a constellation of radio-frequency coils from an imaging zone. The target zone is within the imaging zone. The magnetic resonance imaging system comprises a magnet for generating a magnetic field within the imaging zone. The radio therapy source is adapted for rotating at least partially about the magnet. In some embodiments the X-ray radiation will pass through the magnet or a portion of the magnet. In other embodiments the magnet is designed such as a split magnet such that the X-ray radiation can avoid hitting the magnet.

The medical instrument further comprises a processor for controlling the medical instrument. The medical instrument further comprises a memory for storing an X-ray transmission model of an accessory and for storing machine-executable instructions for execution by the processor. Execution of the instructions causes the processor to receive a treatment plan for eradiating the target zone. A treatment plan as used herein is data which specifies the treatment of a particular region or regions of a subject. A treatment plan may also contain anatomical landmarks which can be used to register the treatment plan to medical images such as a magnetic resonance image. Execution of the instructions further causes the processor to modify the treatment plan in accordance with the X-ray transmission model. As the X-ray source generates X-rays as it passes through the accessory there may be critical components which should not be irradiated and/or the radio-frequency coil may also attenuate the X-rays. The treatment plan can also be modified to avoid destroying sensitive portions of the radio-frequency coil and/or also to ensure that the radiation of the target zone is performed accurately. Execution of the instructions further causes the processor to acquire the magnetic resonance data using the magnetic resonance imaging system. Execution of the instructions further causes the processor to reconstruct a magnetic resonance image from the magnetic resonance data. Execution of the instructions further causes the processor to register a location of the target zone in the magnetic resonance image. That is to say the target zone is located in the magnetic resonance image. This enables the treatment plan to be registered to the coordinate system of the magnetic resonance imaging system and the LINAC. Execution of the instructions further cause the processor to generate control signals in accordance with the location of the target zone and the X-ray transmission model. Detailed control signals for controlling the operation of the LINAC have then been generated. Execution of the instructions further cause the processor to control the LINAC to irradiate the target zone using the control signals. Embodiments of the invention may be beneficial because it may avoid damaging the accessory and/or providing more accurate radiation of the target zone by accounting for attenuation of the X-rays through the accessory.

In another embodiment the accessory is a radio-frequency coil. The radio-frequency coil is attached to the magnetic resonance imaging system with a predefined geometry. The control signals are also at least partially generated using the predefined geometry. That is to say the predefined geometry, the location of the target zone and the X-ray transmission model are used to generate the control signals. In this embodiment the radio-frequency coil is attached to the magnetic resonance imaging system such that there is a predefined geometry. In this way the X-ray transmission model has its coordinates defined relative to the coordinates of the medical instrument in a known fashion.

In another embodiment the radio-frequency coil comprises a first coil under a subject support.

In another embodiment the radio-frequency coil comprises a fixed posterior coil under a subject support.

In another embodiment the radio-frequency coil comprises a second coil fixed above a subject support.

In another embodiment the radio-frequency coil comprises an anterior coil fixed above a subject support.

In another embodiment the second coil comprises a height adjustment mechanism for adjusting the height of the second coil relative to the subject. This embodiment may be beneficial because the second coil can be pre-positioned in the bore of the magnet. After the subject has been placed or positioned inside the magnet the second coil can then be adjusted to an optimal distance between the magnet and the subject. This maintains the effectiveness of the coil while maintaining the predefined geometry with respect to the magnet.

In another embodiment the radio-frequency coil comprises a fixed system coil.

In another embodiment the radio-frequency comprises a fixed system coil with an adapted posterior coil portion.

In another embodiment the radio-frequency coil is operable for being attached to the subject.

In another embodiment the accessory is any one of the following: a radio frequency coil, a transmit coil and/or a receive coil, a mask, a breathing tube, a sensor, a patient support, a fixation element, an electrode, and headphones.

In another embodiment the accessory comprises magnetic resonance fiducial markers. Execution of the instructions further causes the processor to identify an accessory in the magnetic resonance image. The control signals are generated at least partially using the accessory location. This embodiment may be beneficial because if the accessory is attached to a subject the location of the accessory may not be referenced or known relative to the coordinate system of the medical instrument. However, using standard image processing techniques the location of the fiducial markets may be identified in the magnetic resonance image. This enables registering the location of the X-ray transmission model to the coordinate system of the medical instrument.

In another embodiment the coil comprises a cable with a position measuring device. The position measuring device may for example be a potentiometer or potentiometers could be attached to structures to measure the position of the accessory. The position measuring device may also be, for the sake of example be, a shape-sensing fiber. A shape-sensing fiber as used herein is a cable which has shape-sensing technology and can track the position of a cable to a high degree of accuracy along its entire length. For instance Luna Innovations manufactures a shape-sensing cable which may be embedded in cables or attached to such things as surgical tools or other devices. The cable has an optical fiber with many fiber Bragg grating strain sensors along its length. Using an optical frequency domain reflectometry technique permits tens of thousands of sensors with the same nominal reflected wavelength to be read with a very high spatial resolution. This enables the tracking of a position of the cable.

Execution of the instructions further causes the processor to determine a cable path using the shape-sensing fiber. The control signals are generated at least partially using the cable path. In some embodiments the location of the cable path may be used to avoid radiating the cable. In other embodiments the location of the cable path may be used to identify the location or orientation of the accessory. A shape-sensing fiber may also be used to identify the location of other components or sensors in the bore of the magnet. For instance temperature, EEG electrodes, or such things as a breathing tube may have their locations identified which enables the medical instrument to determine their location and avoid radiating them.

In another embodiment the shape-sensing fiber comprises a tip. The tip has a predefined orientation relative to the accessory. The control signals are generated at least partially using the cable path and the predefined orientation.

In another embodiment the control signals are operable for causing the X-ray source to avoid critical components. The critical components could be critical radio-frequency components in some embodiments. This embodiments may be advantageous because the critical components can be avoided which eliminates the possibility of them being damaged by the X-ray source.

In another embodiment the control signals are operable for causing the X-ray source to compensate for the attenuation of the X-ray source by the accessory.

In another embodiment the radio-frequency coil is a transmit coil and/or a receive coil.

In another aspect the invention provides for a computer program product comprising machine-executable instructions for execution by a processor controlling a medical instrument and an X-ray transmission model of a accessory. The medical instrument comprises a LINAC with an X-ray source for directing X-ray radiation at a target zone. The LINAC is adapted for rotating the X-ray source about a rotational point. The medical instrument further comprises the magnetic resonance imaging system for acquiring magnetic resonance data with the accessory from an imaging zone. The target zone is within the imaging zone. The magnetic resonance imaging system comprises a magnet for generating a magnetic field within the imaging zone. The X-ray source is adapted for rotating at least partially about the magnet. Execution of the instructions causes the processor to receive a treatment plan for eradiating the target zone.

Execution of the instructions further causes the processor to modify the treatment plan in accordance with the X-ray transmission model. Execution of the instructions further causes the processor to acquire the magnetic resonance data using the magnetic resonance imaging system. Execution of the instructions further causes the processor to reconstruct the magnetic resonance image from the magnetic resonance data. Execution of the instructions further causes the processor to register a location of the target zone in the magnetic resonance image. Execution of the instructions further causes the processor to generate control signals in accordance with the location of the target zone and the X-ray transmission model. Execution of the instructions further causes the processor to control the LINAC to irradiate the target zone using the control signals.

In another aspect the invention provides for a method of operating a medical instrument. The medical instrument comprises a LINAC with an X-ray source for directing an X-ray radiation at a target source. The LINAC is adapted for rotating the X-ray source about a rotational point. The medical instrument further comprises a magnetic resonance imaging system for acquiring magnetic resonance data with the radio-frequency coil from an imaging zone. The target zone is within the imaging zone. The magnetic resonance imaging system comprises a magnet for generating a magnetic field within the imaging zone. The X-ray source is adapted for rotating at least partially about the magnetic. The method comprises the step of receiving a treatment plan for radiating the target zone.

The method further comprises the step of modifying the treatment plan in accordance with the X-ray with an X-ray transmission model. The method further comprises acquiring the magnetic resonance data using the magnetic resonance imaging system. The method further comprises reconstructing a magnetic resonance image from the magnetic resonance data. The method further comprises registering a location of the target zone in the magnetic resonance image. The method further comprises generating control signals in accordance with the location of the target zone and the X-ray transmission model. The method further comprises controlling the LINAC to irradiate the target zone using the control signals.

It is understood that one or more of the aforementioned embodiments of the invention may be combined as long as the combined embodiments are not mutually exclusive.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
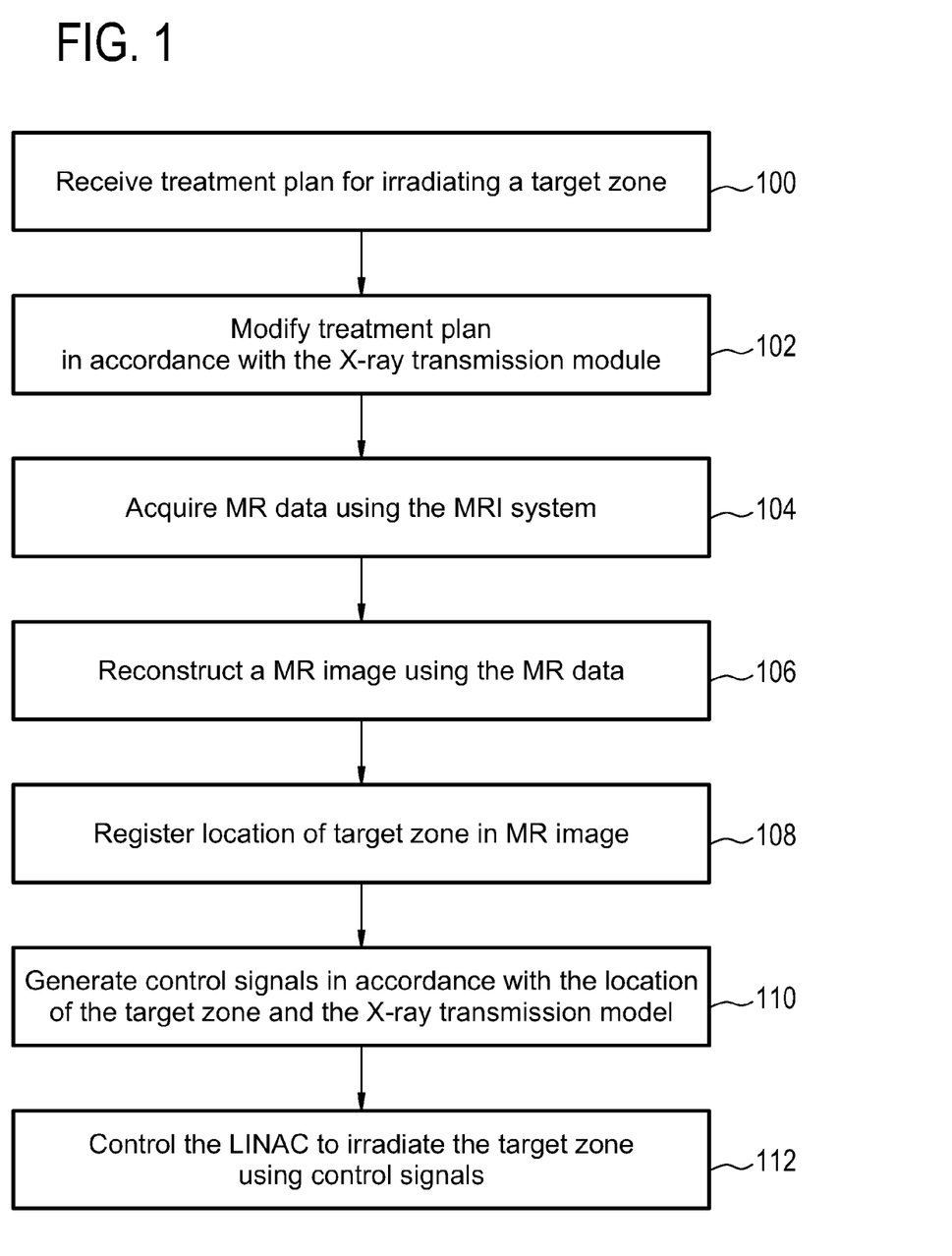
FIG. 1 shows a flow diagram which illustrates a method according to an embodiment of the invention.

FIG. 1 shows a flowchart which illustrates a method according to an embodiment of the invention. In block 100 a treatment plan was received which is descriptive of how to irradiate a target zone. Next in step 102 the treatment plan is modified in accordance with an X-ray transmission model of an accessory. Next in step 104 magnetic resonance data is acquired using a magnetic resonance imaging system. In step 106 a magnetic resonance image is reconstructed from the magnetic resonance data. Next in step 108 a location of the target zone is registered in the magnetic resonance image. In step 110 control signals are generated in accordance with the location of the target zone and the X-ray transmission model for controlling a LINAC. Finally in step 112 a LINAC is controlled to irradiate the target zone using the control signals.

Figure 2:
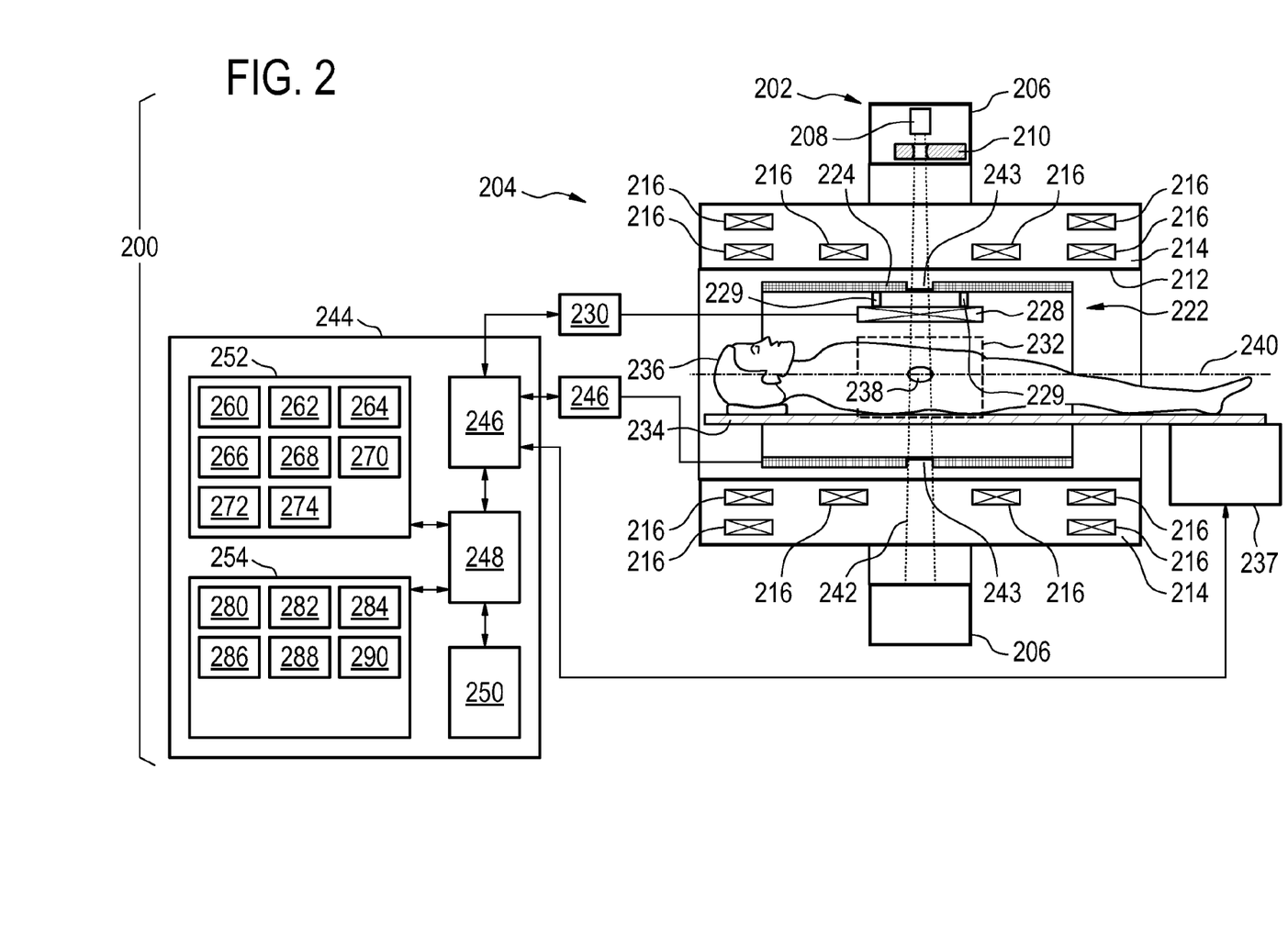
FIG. 2 illustrates a medical instrument according to an embodiment of the invention.

FIG. 2 shows an embodiment of a medical apparatus 200 according to the invention. The medical apparatus 200 comprises a LINAC 202 and a magnetic resonance imaging system 204. The LINAC 402 comprises a gantry 206 and a X-ray source 208. The gantry 206 is for rotating the X-ray source 208 about an axis of gantry rotation 240. Adjacent to the X-ray source 208 is an adjustable collimator 210. The adjustable collimator 210 may for instance have adjustable plates for adjusting the beam profile of the X-ray source 208. The adjustable collimator may, for example, be a multi-leaf collimator. The magnetic resonance imaging system 204 comprises a magnet 212.

It is also possible to use permanent or resistive magnets. The use of different types of magnets is also possible for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils. The magnet 212 shown in this embodiment is a standard cylindrical superconducting magnet. The magnet 212 has a cryostat 214 with superconducting coils within it 216. The magnet 412 has a bore 422. Within the bore 222 of the cylindrical magnet 212 there is an imaging zone where the magnetic field is strong and uniform enough to perform magnetic resonance imaging.

Within the bore 222 of the magnet 212 is a magnetic field gradient coil 224 for acquisition of magnetic resonance data to spatially encode magnetic spins within an imaging zone of the magnet. The magnetic field gradient coil 224 is connected to a magnetic field gradient coil power supply 226. The magnetic field gradient coil 224 is intended to be representative, to allow radiation to pass through without being attenuated it will normally be a split-coil design. Typically magnetic field gradient coils contain three separate sets of coils for spatially encoding in three orthogonal spatial directions. The magnetic field gradient power supply 226 supplies current to the magnetic field gradient coils. The current supplied to the magnetic field coils is controlled as a function of time and may be ramped or pulsed.

There is a radio frequency coil 228 connected to a transceiver 230. The radio frequency coil 228 is adjacent to an imaging zone 232 of the magnet 212. The imaging zone 232 has a region of high magnetic field and homogeneity which is sufficient for performing magnetic resonance imaging. The radio frequency coil 228 may is for manipulating the orientations of magnetic spins within the imaging zone and for receiving radio transmissions from spins also within the imaging zone. The radio frequency coil 228 may also be referred to as an antenna or channel. The radio frequency coil 228 may contain multiple coil elements. The radio frequency antenna may also be referred to as a channel.

The radio frequency coil 228 and radio frequency transceiver 230 may be replaced by separate transmit and receive coils and a separate transmitter and receiver. It is understood that the radio frequency coil and the radio frequency transceiver are simply representative. The radio frequency antenna is intended to also represent a dedicated transmit antenna and a dedicated receive antenna. Likewise the transceiver may also represent a separate transmitter and receivers.

Also within the bore of the magnet 222 is a subject support 234 for supporting a subject 236. The subject support 234 may be positioned by a mechanical positioning system 237. Within the subject 236 there is a target zone 238. The axis of gantry rotation 240 is coaxial in this particular embodiment with the cylindrical axis of the magnet 212. The subject support 234 has been positioned such that the target zone 238 lies on the axis 240 of gantry rotation. The X-ray source 208 is shown as generating a radiation beam 242 which passes through the collimator 210 and through the target zone 238. As the radiation source 208 is rotated about the axis 240 the target zone 238 will always be targeted by the radiation beam 242. The radiation beam 242 passes through the cryostat 214 of the magnet. The magnetic field gradient coil 224 has a gap 243 which separate the magnetic field gradient coil into two sections. The gap 243 reduced attenuation of the radiation beam 242 by the magnetic field gradient coil 224. In an alternative embodiment a split or open magnet design is used to reduce the attenuation of the X-ray beam by the magnet 212.

The radio-frequency coil 228 can be seen as being attached to the inside of the bore of the magnet 222 by several mounts 229. In some embodiments the mounts 229 may include a mechanism which allows the raising and lowering of the radio-frequency coil 228. In any case the mounts 229 define the location of the radio-frequency coil 228 relative to the magnet 212.

The transceiver 230, the magnetic field gradient coil power supply 226 and the mechanical positioning system 237 are all shown as being connected to a hardware interface 246 of a computer system 244. The computer system 244 is shown as further comprising a processor 248 for executing machine executable instructions and for controlling the operation and function of the medical apparatus. The hardware interface 246 enables the processor 248 to interact with and control the medical apparatus 200. The processor 248 is shown as further being connected to a user interface 250, computer storage 252, and computer memory 254.

The computer storage 252 is shown as containing a treatment plan 260. The computer storage 252 is further shown as containing an X-ray transmission model 262 of the radio-frequency coil 228. The X-ray transmission model 262 may comprise the location of sensitive components of the radio-frequency coil 228 and also the X-ray transmission properties of the radio-frequency coil 228. The computer storage 252 is further shown as containing a pulse sequence 264. A pulse sequence as used herein is a set of commands used to control various components of the magnetic resonance imaging system 204 to acquire magnetic resonance data 266. The computer storage 252 is shown as containing magnetic resonance data 266 that was acquired using the magnetic resonance imaging system 204.

The computer storage 252 is further shown as containing a magnetic resonance image 268 that was reconstructed from the magnetic resonance data 266. The computer storage 252 is further shown as containing an image registration 270 of the magnetic resonance image 268. The image registration 270 registers the location of the image relative to the magnetic resonance imaging system 204 and the LINAC 202. The computer storage 252 is further shown as containing the location 272 of the target zone 238. This was identified in the magnetic resonance image 268. The computer storage 252 is further shown as containing control signals 274. The control signals 274 are control signals which are used to control the LINAC 202 to irradiate the target zone 238.

The computer memory is shown as containing a control module 280. The control module contains computer-executable code which enables the processor 248 to control the operation and function of the medical apparatus 200. For instance the control module 280 may use the pulse sequence 264 to acquire the magnetic resonance data 266. The control module 280 may also use the control signals 274 to control the LINAC 202. The computer memory 254 is further shown as containing a treatment plan modification module 282. The treatment plan modification module 282 modifies the treatment plan 260 using the information contained in the X-ray transmission model 262. The computer memory 254 is shown as further containing an image reconstruction module 284. The image reconstruction module 284 contains code which enables the processor 248 to reconstruct the magnetic resonance image 268 from the magnetic resonance data 266.

The computer memory 254 is shown as further containing an image registration module 286. The image registration module 286 contains code which enables the processor 248 to generate the image registration 270 in the location of the target zone 272 using the magnetic resonance image 268. The computer memory 254 is shown as further containing a target zone location module 288. The target zone location module 288 contains code which enables the processor 248 to generate the location of the target zone 272 using the image registration 270. The computer memory 254 is further shown as containing a control signal generation module 290. The control signal generation module 290 contains code which enables the processor 248 to generate the control signals 274 from the treatment plan 260 and the location of the target zone 272. The treatment plan 260 after it has been modified in accordance with the X-ray transmission module is used.

Figure 3:
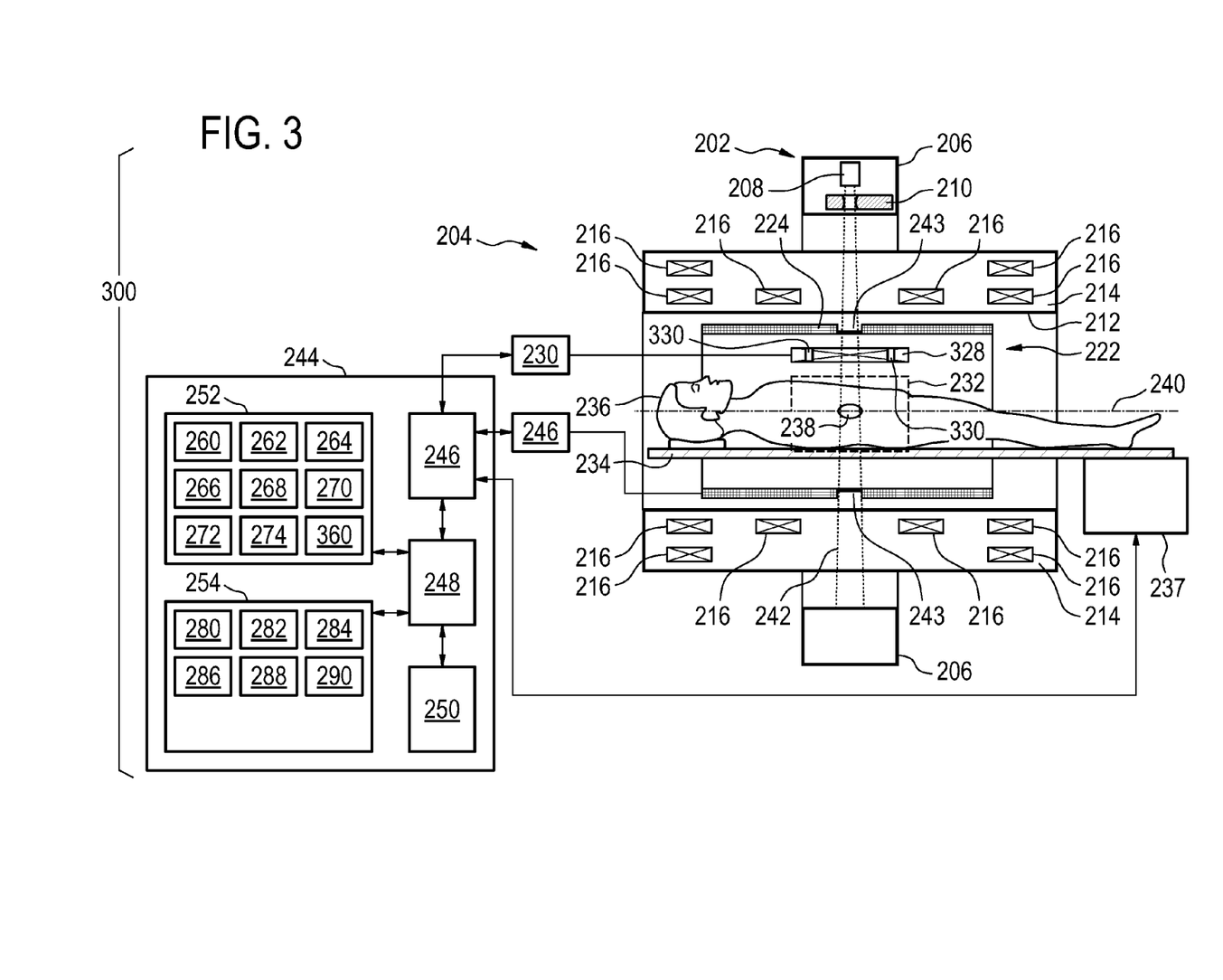
FIG. 3 illustrates a medical instrument according to a further embodiment of the invention.

FIG. 3 shows a medical apparatus according to a further embodiment of the invention. The embodiment shown in FIG. 3 is similar to that shown in FIG. 2 with the exception that the radio-frequency coil 328 in this embodiment is not mounted or fixed inside of the bore 222 of the magnet 212. Instead the radio-frequency coil 328 has several fiducial markers 330. The radio-frequency coil 328 and at least the fiducial markers 330 are located within the imaging zone 232. In this embodiment the image registration module 286 was used to detect the location of the fiducial markers 330 in the magnet resonance image 268 to generate accessory locations 360, which is stored in the computer storage 252. In this embodiment the control signal generation module 290 additionally uses the accessory location 360.

In conventional radiation therapy the radiation pattern is planned based on stationary images showing the patient anatomy including the targeted therapy region. The therapy is executed assuming that the patient anatomy corresponds to the situation during the time of the planning imaging typically taken earlier than the execution of the therapy. Often the human anatomy is not stationary, thus additional margins are added to the therapy so that the targeted region is sufficiently covered. This increases the radiation dose of the healthy tissue. One method to target the dose more accurately is to do the radiation therapy under image guidance (IMRT).

In many cases imaging or therapy requires that there are accessories in the volume where the radiation is going through. An example of such accessory is anatomy specific receive coil used in the MR imaging. These coils are preferably located close to anatomy to be imaged/tracked to enable sufficient image quality. Location of the coil typically varies from patient to patient and from therapy to therapy. Accessories may be sensitive to radiation and/or may affect the radiation. Thus it is advantageous know the location of the radiation affecting parts to take them into account in the therapy. This invention proposes solution how to trace the location of such accessories and take them into account in the image guide radiation therapy.

In FIG. 3 the radio-frequency coil 228, or other accessory, has one or more fiducial markers 330. These markers are imaged and their positions are evaluated. Based on the positions of the fiducial markers 330 and the X-ray transmission model the location of the full accessory is calculated with respect to the image coordinates and therapy coordinates. The information of the accessory location is used to adjust the therapy. Such adjustments may comprise:

steering radiation beam direction and radiation source location so that the sensitive part of the accessory is not exposed to radiation;

steering radiation dose and direction so that the effect of the defined accessory location and interference of the accessory to the radiation beam is compensated;

instructing user to reposition accessory or patient so that the interference of the accessory with the radiation beam is reduced and therapy execution optimized;

automatically (e.g. using motorized table positioning) repositioning accessory or patient so that the interference of the accessory with the radiation beam is reduced; and detection can be real-time to take into account the accessory location during the therapy and to adjust the therapy execution based on the accessory location.

Implementations of the embodiment shown in FIG. 3 may have one or more of the following features:

1. Accessory or radio frequency coil has fiducial markers which are visible for the imaging system
    a. There is enough fiducial markers to define accessory position, orientation and shape with respect imaging coordinates
        i. Single point like fiducial could be enough if the orientation of the accessory is fixed with respect imaging system.
        ii. Two point like fiducials or one line like fiducial are sufficient to determine position and orientation of cylindrical symmetric accessory or accessory that has one rotation fixed.
        iii. Three point like fiducials or one fiducial with suitable 3-dimensional shape is sufficient to determine three position and three orientation coordinates of the accessory
        iv. There can be more fiducial markers to enable determining shape changes of non-rigid accessories or to make position and orientation detection more robust or to expand traceability to cover larger area (i.e. to guarantee that sufficient amount of fiducials are in the imaging system field of view).
    b. Fiducial markers can be passive, i.e., materials that are just visible for the used imaging modality.
        i. In case of MRI imaging the fiducials can be for example capsules filled with suitable MRI visible material. Detected nucleus can be 1H or another MRI sensitive nucleus.
    c. Fiducial markers can be active, i.e., such that they are visible only when activated
        i. In case of MRI imaging active marker could be marker that is surrounded by dedicated fiducial marker coil.
2. Imaging device scans images which can be used to define the position of the accessory
    a. Imaging sequence can be 3-dimensional showing all fiducial markers separately
    b. Imaging sequence can be 2-dimensional with multiple slices showing all fiducials separately
    c. Imaging sequence can consist multiple 2-dimensional projections from which the location of the fiducials are identified
    d. Imaging sequence can consist of multiple 1-dimensional projections from which the fiducials are identified
    e. Imaging modality can be MRI.
3. Control software has a model of the accessory that includes
    a. information of the fiducial marker positions
    b. information of the geometrical shape of the accessory
    c. information of the different parts of accessory effect on the radiation (e.g. spatial attenuation)
    d. information of the radiation sensitivity of the different parts of the accessory
4. Control software evaluates the position of the accessory from the image information with respect to the radiation therapy beam direction, and based on the information it can a. switch off or reduce radiation if it goes through accessory region that is sensitive to radiation
b. Calculates the attenuation of the accessory for the beam and
   i. Either increase the radiation to compensate the effect of attenuation
   ii. Or takes the attenuation into account when estimating the delivered radiation dose in the different parts of the anatomy
c. Instructs user to reposition the accessory or patient so that it does not interfere with the planned radiation therapy or minimizes the interference with the therapy.
   i. Alternatively system can do repositioning automatically e.g. using motorized couch
d. Detection can be repeated to monitor changes in the accessory location, in particular when the accessory position depends on the patient position.
   i. Repetition of the accessory tracing can be real-time in comparison to the expected motion so that the above corrections can be made "on-the-fly".

Figure 4:
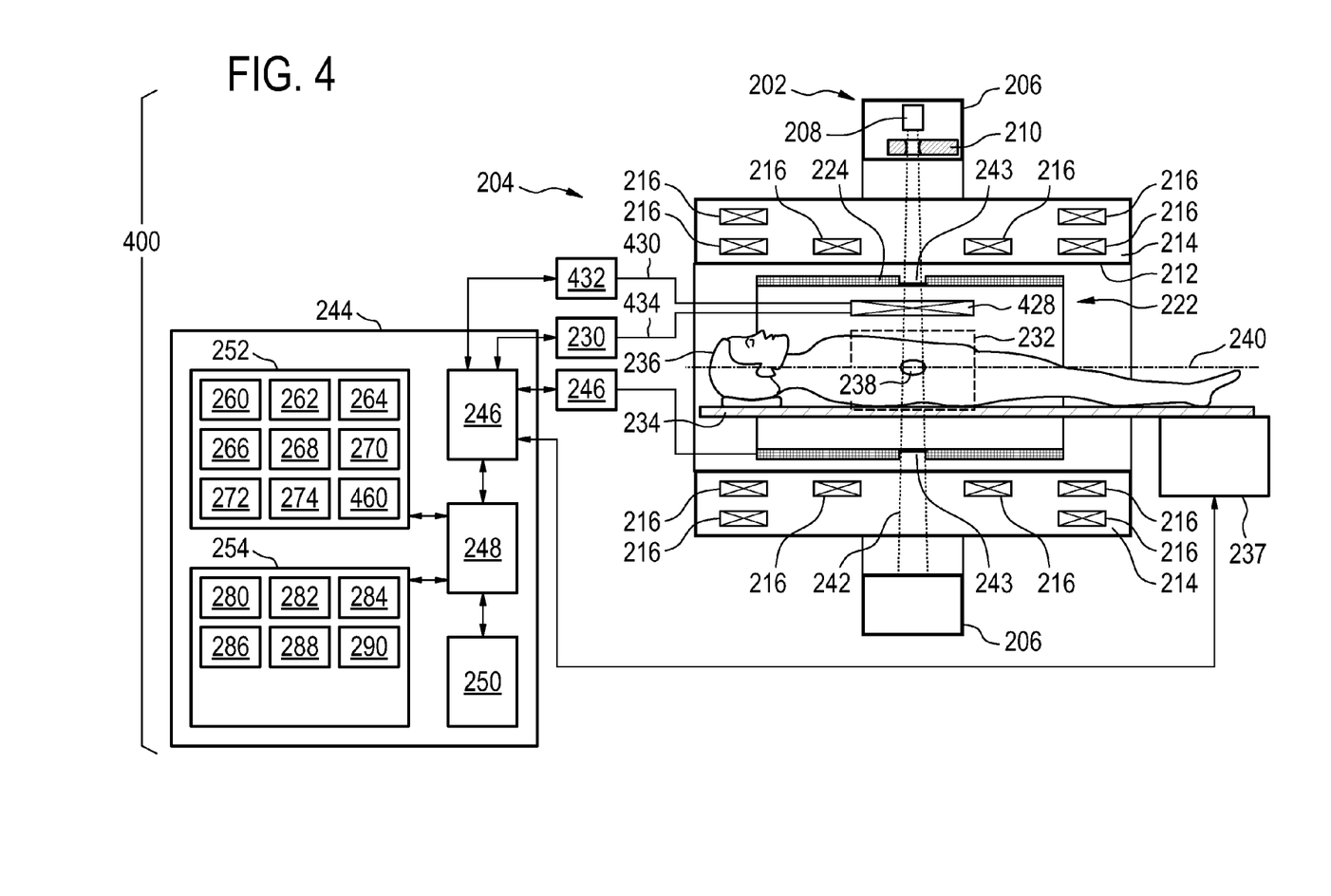
FIG. 4 illustrates a medical instrument according to a further embodiment of the invention.

FIG. 4 shows a further embodiment of a medical apparatus 400 according to an embodiment of the invention. The embodiment shown in FIG. 4 is similar to that shown in FIGS. 2 and 3 except in this embodiment the radio-frequency coil or accessory 428 has its position determined by a mechanical or optical positioning measuring device such as a position potentiometer or a shape-sensing fiber 430. The positioning measuring device is connected to positioning measuring device electronics 432. For instance the shape-sensing fiber electronics 432 may contain the laser for use with the Bragg diffraction gradients within the shape-sensing fiber 430. There is a radio-frequency cable 434 between the transceiver 230 and the radio-frequency coil 428. The positioning measuring device 430 can be attached to the radio-frequency cable 434. In this way the position of the radio-frequency cable 434 and hence the location and orientation of the radio-frequency coil 428 is known. The positioning measuring device 430 can be attached to the accessory directly 428. The shape-sensing fiber electronics 432 are shown as being connected to the hardware interface 246. The positioning measuring device 432 provides the computer system with a cable path 460. The cable path 460 is shown as being stored in the computer storage 252. In this embodiment the control signal generation module 290 uses the cable path 460 to define the location of the accessory 428 relative to the magnetic resonance imaging system 222 and the LINAC 202.

Embodiments of the invention may provide a way to reduce the degrees of freedom in order to facilitate coil design and coil life expectancy. They may also facilitates the attenuation calculations necessary to calibrate the system for treatment.

Embodiments of the invention may solve one or more of the following problems:
Reduced life expectancy of RF coils
Difficult to determine the attenuation for the LINAC system caused by the RF coil. This is necessary for the (reverse) calculation of the radiation dose.
Difficult coil design
Difficult coil placement
Patient space restrictions Embodiments of the invention may one or more of the following features related to RF coils are positioned with a fixed position with respect to the LINAC system, such that:
a. The coil part that is exposed to radiation (radiation window) is optimized for life expectancy. This could be done e.g. by removing coil electronics sensitive to radiation as much as possible from the radiation window. The parts outside the radiation window don't have to be designed to be insensitive to radiation beams.
b. The coil is still close to the patient for optimal receive (or transmit) behavior
c. The coil is minimized in thickness to allow for as much space as possible in the bore By having a fixed position to the LINAC system, the attenuation relation to the LINAC should be known at all times. This facilitates (reverse) calculation of the right dose deposition for radiation treatment. FIGS. 5 through 8 illustrate several embodiments where the position of the radio frequency coil is fixed relative to the position of the LINAC system.

Figure 5:
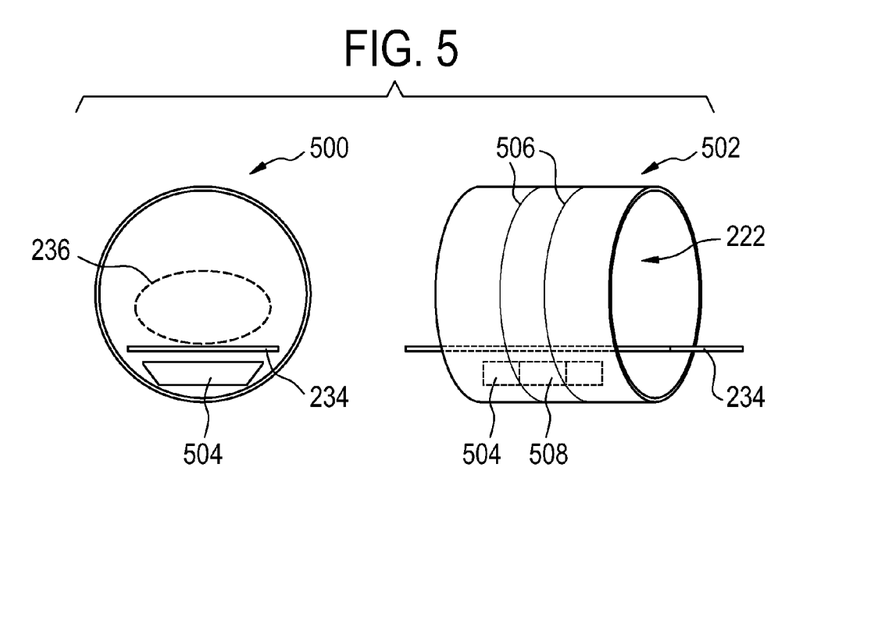
FIG. 5 shows an idealized medical apparatus with a posterior coil beneath a subject support.

FIG. 5 shows an end view 500 and a side view 502 of an idealized medical apparatus. A subject support 234 for supporting a subject 236 is visible. Beneath the subject support 234 there is a posterior coil 504 with a fixed location within the bore 222 of the medical apparatus 500, 502. The side view 502 shows a radiation window 506 or region where radiation enters into the bore 222. The area marked 508 is a region of the fixed posterior coil 504 which is exposed to radiation.

Figure 6:
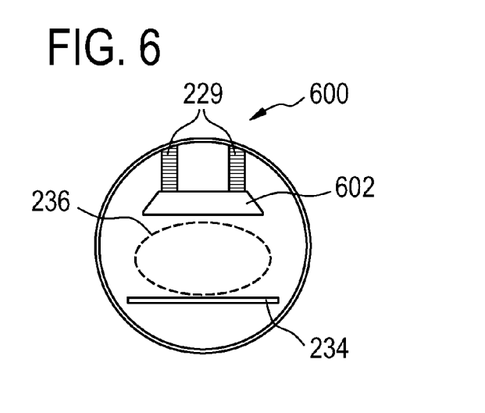
FIG. 6 shows an idealized medical apparatus with a fixed anterior coil mounted above a subject support.

FIG. 6 shows an end view of an idealized medical apparatus. The subject 236 is supported by a subject support 234. In this case there is a fixed anterior coil 602 mounted above the subject 236 using several mounts 229.

Figure 7:
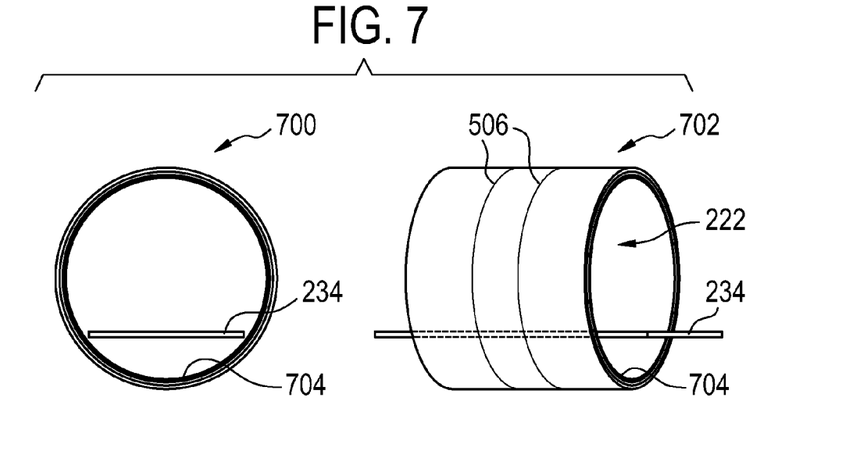
FIG. 7 shows an idealized medical apparatus with a system transmit and/or receive coil within the bore of the magnet.

FIG. 7 shows an end view 700 and side view 702 of an idealized medical apparatus. In this embodiment there is a system transmit and/or receive coil 704 within the bore 222.

Figure 8:
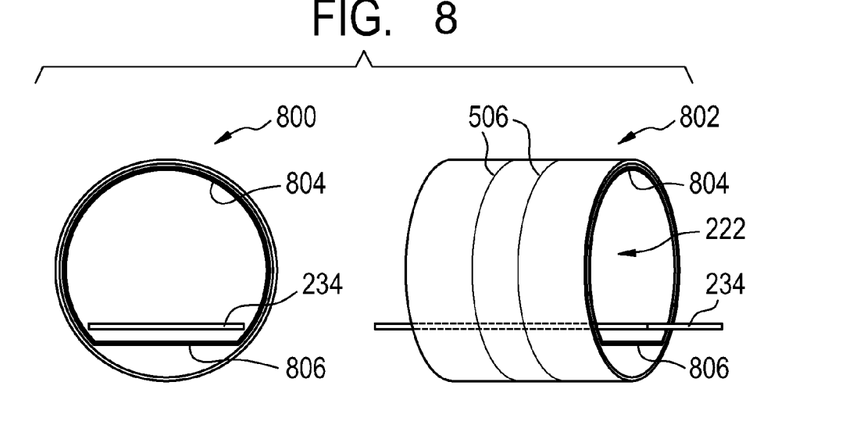
FIG. 8 shows an idealized medical apparatus with a system transmit and/or receive coil with a modified posterior part in the bore of the magnet.

FIG. 8 shows an end view 800 and side view 802 of an idealized medical apparatus. In this embodiment there is again a system transmit and/or receive coil 804 in the bore 222. However, in this embodiment there is a modified posterior part 806. The posterior coil has been incorporated into the system and/or receive coil 804.

In MR guided LINACs, the irradiation beam may pass through coils and support devices (e.g., respiratory or cardiac devices) and their cabling: These items must be positioned freely and into the vicinity of the treatment volume. This requires flexible cables.

Flexible cables may attenuate the X-ray beam in unpredictable ways. Attenuation results in uneven radiation dose to the target volume and/or may damage cables and devices themselves.

Placing an optical shape sensing catheter inside/attaching the catheter to cabling and/or the device can be used to estimate cable and device position with good accuracy. The optical electronics can be located outside the beam and the positioning coordinate system fixed to a-priori known location in LINAC coordinate system.

The position information can be fed to dose planning with known cable/device attenuation so that the beam shape and power can be adjusted to take into account the blocking items/avoid sensitive device parts.

Another embodiment is to use the position data to avoid cabling altogether by preventing irradiation at angles where irradiation would collide with cabling or device.

Figure 9:
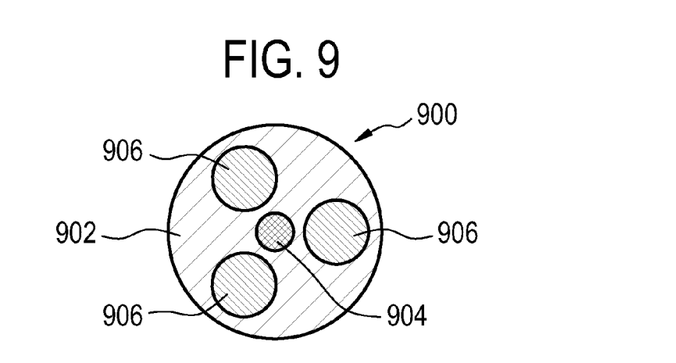
FIG. 9 shows an embodiment of a shape-sensing cable.

A simplest case is to replace cable core with an optical sensor to localize the cable is illustrated in FIG. 9. FIG. 9 shows an embodiment of a shape-sensing cable 900 according to the invention. This cable has a cable body 902. Within the cable body 902 there is an embedded shape-sensing fiber 904. Surrounding the shape-sensing fiber 904 there are several wires 906. This for instance could be used for a cable between a radio-frequency antenna and a transceiver. In other embodiments the exact position of the shape-sensing fiber 904 relative to the wires 906 may be different. For instance the shape-sensing fiber 904 may be applied to an outer surface of the cable 900. There also may be more or fewer wires 906 and also the wires 906 may be replaced with such things as tubes for transmitting fluids or liquids and/or fiber optic cables.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS 200 medical apparatus
202 LINAC
204 magnetic resonance imaging system
206 gantry
208 X-ray source
210 adjustable collimator
212 magnet
214 cryostat
216 superconducting coil
222 bore
224 magnetic field gradient coil
226 magnetic field gradient coil power supply
228 radio frequency coil
229 mount
230 transciever
232 imaging zone
234 subject support
236 subject
237 mechanical positioning system
238 target zone
240 axis of gantry rotation
242 radiation beam
443 gap
244 computer system
246 hardware interface
248 processor
250 user interface
252 computer storage
254 computer memory
260 treatment plan
262 x-ray transmission model
264 pulse sequence
266 magnetic resonance data
268 magnetic resonance image
270 image registration
272 location of target zone
274 control signals
280 control module
282 treatment plan modification module
284 image reconstruction module
286 image registration module
288 target zone location module
290 control signal generation module
300 medical apparatus
328 radio frequency coil
330 fudical marker
360 accessory location
400 medical apparatus
428 radio frequency coil
430 shape sensing fiber
432 shape sensing fiber electronics
434 radio frequency cable
460 cable path
500 end view of medical apparatus
502 side view of medical apparatus
504 fixed posterior coil
506 radiation window
508 irradiated region
600 end view of medical apparatus
602 fixed anterior coil
700 end view of medical apparatus
702 side view of medical apparatus
704 system transmit and/or receive coil
800 end view of medical apparatus
802 side view of medical apparatus
804 system transmit and/or receive coil
806 posterior part
900 cable
902 cable body
904 shape sensing fiber
906 wire

The invention claimed is:
1. A medical instrument comprising:
a LINAC with an X-ray source for directing X-ray radiation at a target zone, wherein the LINAC is adapted for rotating the X-ray source about a rotational axis,
a magnetic resonance imaging system for acquiring magnetic resonance data with a radio frequency coil from an imaging zone, wherein the target zone is within the imaging zone, wherein the magnetic resonance imaging system comprises a magnet for generating a magnetic field within the imaging zone, wherein the X-ray source is adapted for rotating at least partially about the magnet;
a processor for controlling the medical instrument;
a memory for storing an X-ray transmission model of an accessory and for storing machine executable instructions for execution by the processor, wherein execution of the instructions causes the processor to:
receive a treatment plan for irradiating the target zone;
modify the treatment plan in accordance with the X-ray transmission model;
acquire the magnetic resonance data using the magnetic resonance imaging system;
reconstruct a magnetic resonance image from the magnetic resonance data;
locate the target zone in the magnetic resonance image;
generate control signals, for controlling the LINAC to irradiate the target zone, in accordance with the location of the target zone and a position, identified within the X-ray transmission model, of a fiducial marker attached to the accessory; and control the LINAC to irradiate the target zone using the control signals.

2. The medical instrument of claim 1, wherein the accessory is the radio frequency coil, wherein the radio frequency coil is attached to the magnetic resonance imaging system with a predefined geometry, wherein the control signals are generated using the predefined geometry.

3. The medical instrument of claim 2, wherein the radio frequency coil comprises a first coil under a subject support.

4. The medical instrument of claim 2, wherein the radio frequency coil comprises a second coil fixed above a subject support.

5. The medical instrument of claim 4, wherein an anterior coil of the radio frequency coil comprises a height adjustment mechanism for adjusting the height of the anterior coil relative to the subject.

6. The medical instrument of claim 2, wherein the radio frequency coil comprises a fixed system coil.

7. The medical instrument of claim 2, wherein the radio frequency coil comprises a fixed system coil with an adapted posterior coil portion.

8. The medical instrument of claim 1, wherein the accessory is any one of the following: a radio frequency coil, a transmit coil, a receive coil, a mask, a breathing tube, a sensor, a patient support, a fixation element, an electrode, and headphones.

9. The medical instrument of claim 1, wherein the accessory is operable for being attached to a subject.

10. The medical instrument of claim 9, wherein the accessory comprises magnetic resonance fiducial markers, wherein execution of the instructions further causes the processor to identify an accessory location in the magnetic resonance image, wherein the control signals are generated at least partially using the accessory location.

11. The medical instrument of claim 9, wherein the accessory comprises a positioning measuring device, wherein execution of the instructions further causes the processor to identify an accessory location or to determine a cable path using the positioning measuring device, wherein the control signals are generated at least partially using the accessory location.

12. The medical instrument of claim 11, wherein the positioning measuring device is a shape sensing fiber comprising a tip, wherein the tip has a predefined orientation relative to the radio frequency coil, and wherein the control signals are generated at least partially using the cable path and the predefined orientation.

13. The medical instrument of claim 1, wherein the control signals are operable for causing the x-ray source to avoid a component of the accessory.

14. The medical instrument of claim 13, wherein the control signals are operable for causing the x-ray source to compensate for attenuation of the accessory by steering radiation dose and direction.

15. The medical instrument of claim 1, wherein the control signals are generated, based upon the fiducial marker position, so that the processor's control of the LINAC directs the X-ray radiation so as to prevent exposure of a portion of the accessory to the X-ray radiation.

16. The medical instrument of claim 1, wherein the control signals are generated, based upon the fiducial marker position, so that the processor's control of the LINAC compensates for the accessory's interference of the X-ray radiation to the target zone.

17. The medical instrument of claim 1, wherein:

the medical instrument further comprises a repositioning accessory that repositions a patient under control of the processor and in accordance with the control signals, and the control signals are generated, based upon the fiducial marker position, so that the processor's control of the repositioning accessory repositions the patient to reduce the accessory's interference of the X-ray radiation to the target zone.

18. The medical instrument of claim 1, wherein execution of the instructions further causes the processor to:

determine whether the accessory is incorrectly positioned based upon the fiducial marker position, and provide an instruction for repositioning the accessory or a patient based upon the position determination and the fiducial marker position.

19. A non-transitory computer-readable program product comprising machine executable instructions for execution by a processor controlling a medical instrument and an X-ray transmission model of a radio frequency coil, wherein the medical instrument comprises a LINAC with an X-ray source for directing X-ray radiation at a target zone, wherein the LINAC is adapted for rotating the X-ray source about a rotational point, wherein the medical instrument further comprises a magnetic resonance imaging system for acquiring magnetic resonance data with the radio frequency coil from an imaging zone, wherein the target zone is within the imaging zone, wherein the magnetic resonance imaging system comprises a magnet for generating a magnetic field within the imaging zone, wherein the X-ray source is adapted for rotating at least partially about the magnet, wherein execution of the instructions causes the processor to:

receive a treatment plan for irradiating the target zone;

modify the treatment plan in accordance with the X-ray transmission model;

acquire the magnetic resonance data using the magnetic resonance imaging system;

reconstruct a magnetic resonance image from the magnetic resonance data;

locate the target zone in the magnetic resonance image;

generate control signals, for controlling the LINAC to irradiate the target zone, in accordance with the location of the target zone and a position, identified within the X-ray transmission model, of a fiducial marker attached to the accessory; and control the LINAC to irradiate the target zone using the control signals.

* * * * *